United States Patent [19]
Schulz

[11] Patent Number: 6,130,241
[45] Date of Patent: Oct. 10, 2000

[54] INSECT-REPELLENT FORMULATIONS

[75] Inventor: Darren John Schulz, Sandwich, United Kingdom

[73] Assignee: Pfizer Inc., New York, N.Y.

[21] Appl. No.: 09/147,796

[22] PCT Filed: Sep. 9, 1997

[86] PCT No.: PCT/EP97/04964

§ 371 Date: Mar. 10, 1999

§ 102(e) Date: Mar. 10, 1999

[87] PCT Pub. No.: WO98/13345

PCT Pub. Date: Apr. 2, 1998

[30] Foreign Application Priority Data

Sep. 26, 1996 [GB] United Kingdom ............... 9620049

[51] Int. Cl.[7] ........................... A01N 43/38; C07D 209/52
[52] U.S. Cl. ........................... 514/421; 514/919; 548/513; 424/405; 424/DIG. 10
[58] Field of Search ............... 548/513; 514/421, 514/919; 424/405, DIG. 10

[56] References Cited

U.S. PATENT DOCUMENTS 4,183,857 1/1980 Kollmeyer ............... 548/513

FOREIGN PATENT DOCUMENTS 1770674 2/1970 Germany.
1598095 12/1977 United Kingdom.
8704594 1/1987 WIPO.

OTHER PUBLICATIONS

Poulter et al., Tetrahedron Letters, 1971, 25, 2255–2258.
Chemical Abstracts, Columbus, Ohio, US, vol. 99, 1983, Sep. 26, No. 13, 100966g.
Tufariello et al., Tetrahedron Letters, vol. 28, No. 3, pp. 267–270, 1987.

*Primary Examiner*—Fiona T. Powers
*Attorney, Agent, or Firm*—Peter C. Richardson; Gregg C. Benson; Robert T. Ronau

[57] ABSTRACT

The invention provides an insect- or acarid-repellent formulation comprising a compound of formula (I), wherein R represents straight or branched chain $C_{2-10}$ alkyl, straight or branched chain $C_{2-10}$ alkenyl, or straight or branched chain $C_{2-10}$ alkynyl, which groups are optionally substituted by one or more groups selected from halogen, $C_{4-8}$ cycloalkyl and $C_{4-8}$ cycloalkenyl; and a suitable adjuvant, diluent or carrier.

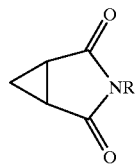

(I)

21 Claims, No Drawings

INSECT-REPELLENT FORMULATIONS

CROSS REFERENCE TO RELATED APPLICATIONS

This application is the National Stage of International Application No. PCT/EP/04964, filed Sep. 9, 1997, designating the United States.

This invention relates to insect- and acarid-repellent formulations, novel compounds for use in such formulations, and methods for repelling insects and acarids.

International patent application WO 87/04594 indicates a group of 1-substituted azacycloalkanes to be useful as insect repellents (see pages 51 and 52).

Japanese Patent Applications 59031702, 58120878, 58072504 and 58072503 claim a group of 1-substituted azacycloalkenes as insect repellents.

Japanese Patent Applications 7118112, 7046955, 6263605, 4225902 and 4036205, and European Patent Application EP 525893 disclose tricyclic azacycloalkanes indicated as insect repellents.

3-n-Butyl-3-azabicyclo[3.1.0]hexane-2,4-dione is disclosed as a chemical intermediate by Tufariello et al, Tetrahedron Letters, Vol 28, No 3, pp 267–270, 1987. 3-n-Octyl-3-azabicyclo[3.1.0]hexane-2,4-dione has been made available on a non-confidential basis.

According to the present invention, there is provided an insect- or acarid-repellent formulation comprising a compound of formula I,

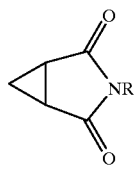

I wherein R represents straight or branched chain $C_{2-10}$ alkyl, straight or branched chain $C_{2-10}$ alkenyl, or straight or branched chain $C_{2-10}$ alkynyl, which groups are optionally substituted by one or more groups selected from halogen, $C_{4-8}$ cycloalkyl and $C_{4-8}$ cycloalkenyl;
and a suitable adjuvant, diluent or carrier.

The formulations of the invention may have the advantage that they are more potent or longer acting than those of the prior art. The nature of the compound of formula I may also confer a pleasant odour on the formulation to humans.

Preferred formulations include those in which:
(a) R represents straight chain $C_{2-10}$ alkenyl (for example 6-hepten-1-yl);
(b) R represents straight chain $C_{2-10}$ alkyl (for example $C_8H_{17}$), optionally substituted by chlorine; and
(c) R comprises a $C_{4-6}$ cycloalkyl group (for example R represents 2-cyclohexylethyl).

"Halogen" means fluorine, chlorine, bromine and iodine. Fluorine and chlorine are of particular interest.

According to the invention there is also provided a compound of formula I, as defined above, with the proviso that R does not represent n-butyl or n-octyl.

The invention further provides a method of repelling insects or acarids, which comprises applying a compound of formula I, as defined above, to the exterior of a mammal. The mammal may be a human, a companion animal (for example a dog or a cat) or a livestock animal. Insects of particular interest are mosquitoes, gnats and midges. Acarids of particular interest are ticks. Preferably, the compound of formula I will be applied in a formulation as defined above.

In addition, the invention provides a process for the production of a compound of formula I, as defined above, with the proviso that R does not represent n-butyl or n-octyl, which comprises:
(a) reacting the compound of formula II,

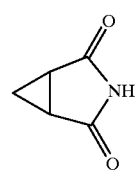

II with a compound of formula RX, wherein R is as defined above, and X is halogen, in the presence of a base;
(b) reacting the compound of formula III,

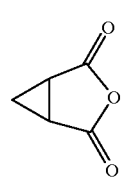

III with a compound of formula $RNH_2$, wherein R is as defined above;
(c) reacting the compound of formula II with diethyl azodicarboxylate, triphenylphosphine and a compound of formula ROH, wherein R is as defined above, in a Mitsunobu reaction; or
(d) reacting a compound of formula IV,

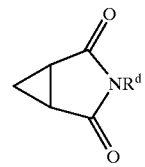

IV in which $R^d$ has the same definition as R above except that it is substituted by OH or oxo, with diethylaminosulfurtrifluoride to give a corresponding compound of formula I in which each OH or oxo group is replaced with one or two fluorine atoms, respectively.

In process (a), the reaction is preferably carried out at or below room temperature in a solvent which does not adversely affect the reaction (for example dimethylformamide). Suitable bases include sodium hydride.

In process (b), the reaction may be carried out in an excess of amine as solvent, at an elevated temperature.

In process (c), the diethyl azodicarboxylate and the triphenyl phosphine are allowed to react together first, below room temperature, and then the compound of formula ROH is added, followed by the compound of formula II. The mixture is then allowed to warm to room temperature. The reaction is preferably carried out in a solvent which does not adversely affect the reaction (for example tetrahydrofuran). The Mitsunobu reaction is described more fully in J Am Chem Soc, 94, 679 (1972).

In process (d), the reaction is preferably carried out at or around room temperature in a solvent which does not adversely affect the reaction (for example dichloromethane).

Compounds of formulae II, III, RX, ROH and $RNH_2$ are either known or are available using known techniques. For example, the synthesis of the compound of formula II is known from Synthetic Communications, 1981, 11(6), 447–54. The synthesis of the compound of formula III is known from Synthesis, 1983, (6), 469–70.

Compounds of formula IV may be prepared by the methods described above for the preparation of compounds of formula I. Compounds of formula IV form a further aspect of the invention.

It will be apparent to those skilled in the art that sensitive functional groups may need to be protected and deprotected during synthesis of a compound of formula I. This may be achieved by conventional techniques, for example as described in 'Protective Groups in Organic Synthesis' by T W Greene and P G M Wuts, John Wiley and Sons Inc, 1991.

The efficacy of the compounds of formula I may be tested in the tests set out below.

Test A—In vitro tick repellence

Test compound, dissolved in a suitable solvent, is applied to the bottom of a test tube. The solvent is then dried off at 32° C. for between 1 to 24 hours. Tick larvae are placed in the mouth of the tube which is then stoppered with cotton wool. The tube is placed beneath a suitable light source and the distance the ticks migrate up the tube is recorded. Activity is expressed as 'percentage repellence' calculated as $(A-B)/A \times 100\%$ where A is the length of the tube and B is the distance the ticks migrate up the tube.

Test B—In vitro mosquito repellence

Test compound, dissolved in a suitable solvent, is applied to a piece of surgical absorbent gauze. The solvent is then dried off at 32° C. for between 1 and 24 hours. The gauze is stretched across the mouth of a plastic tube containing mosquitoes. Repellence is measured by blowing carbon dioxide across the mouth of the tube to provide a 'host seeking stimulus' and counting the number of mosquitoes which alight on the treated gauze. Activity is expressed as 'percentage repellence' calculated as $(C-D)/C \times 100\%$ where C is the number of mosquitoes present in the tube and D is the number which alight on the gauze following carbon dioxide stimulation.

The formulations of the present invention may be prepared from known adjuvants, diluents or carriers using known techniques. For example, when the mammal receiving the formulation is a non-human animal, the formulation may be a pour-on formulation, a spot-on formulation, a spray, a shampoo, a dusting powder, an impregnated strip, a soap, an ear or tail tag or a gel. When the mammal receiving the formulation is a human, the formulation may be a powder, an ointment, a lotion, a wipe, a cream, a soap, an erodible stick or a clothes patch. The formulation may include antioxidants and UV absorbers. Creams and lotions are of particular interest, and may be adapted for application to the skin.

The invention is illustrated by the following examples, in which melting points were determined using a Gallenkamp melting point apparatus and are uncorrected. Nuclear magnetic resonance data were obtained using a Bruker AC300 or AM300. Mass spectral data were obtained on a Finnigan Mat. TSQ 7000 or a Fisons Instruments Trio 1000. The calculated and observed ions quoted refer to the isotopic composition of lowest mass. Infrared spectra were obtained on a Perkin Elmer Paragon 1000 FT-IR spectrometer.

EXAMPLE A1

3-n-Decyl-3-azabicyclo[3.1.0]hexane-2,4-dione

1-Iododecane (1.21 g) was added to a stirred mixture of 3-azabicyclo[3.1.0]hexane-2,4 dione (0.5 g), potassium carbonate (0.62 g) and tetrabutylammonium bromide (1.45 g) in dichloromethane (50 ml) at room temperature and the resulting mixture was stirred for 24 hours. The mixture was filtered and the filtrate was then washed with water (2×100 ml), dried ($MgSO_4$) and evaporated in vacuo to give a brown oil. The oil was purified by column chromatography on silica gel (100 g) using hexane as eluant. Combination and evaporation of the appropriate fractions gave the title compound as a colourless oil.

NMR ($CDCl_3$) 0.8 (t, 3H), 1.0–1.6 (m, 18H), 2.46 (dd, 2H), 3.34 (t, 2H).

MS (thermospray) M/Z [M+$NH_4$] 269, $C_{15}H_{25}NO_2$+$NH_4$ requires 269.

IR (polyethylene) 2940, 2856, 1775, 1710, 1440, 1395.

EXAMPLE A2

3-(4-chlorobut-1-yl)-3-azabicyclo[3.1.0]hexane-2,4-dione

Sodium hydride (0.11 g, 60% dispersion in oil) was added to a stirred solution of 3-azabicyclo[3.1.0]hexane-2,4-dione (0.5 g) and 1-chloro-4-iodooctane (0.98 g) in dry dimethylformamide (50 ml) under a nitrogen atmosphere at room temperature. The resulting mixture was stirred for 48 hours and water (50 ml) was then added dropwise. The aqueous mixture was extracted with dichloromethane (2×200 ml) and the combined organic extracts were then washed with water (2×400 ml), dried ($MgSO_4$) and evaporated in vacuo to give an oil. The oil was purified by chromatography on silica (80 g) using 1:1 ethyl acetate/hexane as eluant to give the title compound as a colourless oil.

NMR ($CDCl_3$) 1.35 (m, 1H), 1.54 (m, 1H), 1.6–1.8 (m, 4H), 2.44 (dd, 2H), 3.39 (t, 2H), 3.53 (t, 2H).

MS (thermospray) M/Z [M+$NH_4$] 219, $C_9H_{12}ClNO_2$+$NH_4$ requires 219.

IR (polyethylene) 2952, 2872, 1770, 1714, 1445, 1397.5

EXAMPLE A3

3-n-Octyl-3-azabicyclo[3.1.0]hexane-2,4-dione

Sodium hydride (1.48 g, 60% in oil) was added to a stirred solution of 3-azabicyclo[3.1.0]hexane-2,4-dione (4.0 g) and 1-iodooctane (8.88 g) in dry dimethylformamide (70 ml) under a nitrogen atmosphere at 0° C. The reaction mixture was stirred at 0° C. for a further 30 minutes and then at room temperature for 16 hours. The mixture was diluted with water (100 ml) and then extracted with ether (150 ml). The organic extract was washed with water (2×70 ml), dried ($MgSO_4$) and evaporated in vacuo to leave a brown oil. The oil was purified by distillation in vacuo (boiling point 146–147° C. @ 0.1 mmHg) to give the title compound as a pale yellow oil.

NMR ($CDCl_3$) 0.83 (t, 3H), 1.15–1.30 (m, 1OH), 1.30–1.40 (m, 2H), 1.40–1.56 (m, 4H), 2.44 (dd, 2H), 3.31 (t, 2H).

MS (thermospray) M/Z [M+$NH_4$] 241, $C_{13}H_{21}NO_2$+$NH_4$ requires 241

IR (polyethylene) 2955, 2916, 2848, 1771, 1715, 1445, 1395

EXAMPLE A4

3-n-Heptyl-3-azabicyclo[3.1.0]hexane-2,4-dione

Sodium hydride (0.11 g) was added to a solution of 3-azabicyclo[3.1.0]hexane-2,4-dione (0.3 g) in dry tetrahydrofuran (10 ml) under a nitrogen atmosphere at room temperature. The suspension was stirred for 5 minutes and 1-iodoheptane (0.61 g) was then added in one portion to the reaction mixture. After stirring for two hours at room temperature, dimethylformamide (5 ml) was added and the reaction mixture was stirred for a further 16 hours at room temperature. The reaction mixture was diluted with dichloromethane and then partitioned with water (20 ml). The aqueous phase was extracted with dichloromethane (20 ml) and the combined organic extracts were washed with water (2×20 ml), dried (MgSO$_4$) and evaporated in vacuo. The residue was purified by chromatography on silica gel (50 g) using 25–30% ethyl acetate/hexane as eluant to give the title compound as a colourless oil.

NMR (CDCl$_3$) 0.88 (t, 3H), 1.12–1.37 (m, 9H), 1.37–1.55 (m, 3H), 2.45 (dd, 2H), 3.34 (t, 2H)

MS (thermospray) M/Z [M+NH$_4$] 227, C$_{12}$H$_{19}$NO$_2$+NH$_4$ requires 227

IR (polyethylene) 2956, 2917, 2848, 1771, 1715

EXAMPLE A5

3-[2-(Cyclohexyl)ethyl]-3-azabicyclo[3.1.0]hexane-2,4-dione

Sodium hydride (0.11 g) was added to a solution of 3-azabicyclo[3.1.0]hexane-2,4dione (0.3 g) and 1-bromo-2-cyclohexylethane (0.52 g) in dimethylformamide (5 ml) and the resulting mixture was stirred at room temperature under a nitrogen atmosphere for 16 hours. The mixture was diluted with water (15 ml) and then extracted with toluene (20 ml). The organic extract was washed with water (15 ml), dried (MgSO$_4$) and evaporated in vacuo. The residue was purified by Kugelrohr distillation (boiling point 130–140° C. @ 0.1 mmHg) to give the title compound as a colourless oil.

NMR (CDCl$_3$) 0.78–1.78 (m, 15H), 2.43 (dd, 2H), 3.34 (t, 2H)

MS (thermospray) M/Z [M+NH$_4$] 239, C$_{13}$H$_{19}$NO$_2$+NH$_4$ requires 239

IR (polyethylene) 2915, 2848, 1771, 1714

EXAMPLE A6

3-(2-Ethylhex-1-yl)-3-azabicyclo[3.1.0]hexane-2,4-dione

Sodium hydride (0.11 g) was added to a solution of 3-azabicyclo[3.1.0]hexane-2,4-dione (0.3 g) and 1-bromo-2-ethylhexane (0.52 g) in dimethylformamide (5 ml) and the resulting mixture was stirred at room temperature under a nitrogen atmosphere for 16 hours. The mixture was diluted with water (15 ml) and then extracted with toluene (20 ml). The organic extract was washed with water (15 ml), dried (MgSO$_4$) and evaporated in vacuo. The residue was purified by Kugelrohr distillation (boiling point 140–160° C. @ 0.1 mmHg) to give the title compound as a colourless oil.

NMR (CDCl$_3$) 0.80–0.95 (m, 6H), 1.05–1.40 (m, 9H), 1.51 (m, 1H), 1.56–1.70 (m, 1 H), 2.45 (dd, 2H), 3.25 (d, 2H)

MS (thermospray) M/Z [M+H] 224, C$_{13}$H$_{21}$NO$_2$+H requires 224

IR (polyethylene) 2915, 2848, 1777, 1715

EXAMPLE A7

3-(7-Octenyl)-3-azabicyclo[3.1.0]hexane-2,4-dione

Sodium hydride (0.11 g) was added to a solution of 3-azabicyclo[3.1.0]hexane-2,4dione (0.3 g) and 7-octenyl bromide (0.52 g) in dimethylformamide (5 ml) and the resulting mixture was stirred at room temperature under a nitrogen atmosphere for 16 hours. The mixture was diluted with water (15 ml) and then extracted with toluene (20 ml). The organic extract was washed with water (15 ml), dried (MgSO$_4$) and evaporated in vacuo. The residue was purified by Kugelrohr distillation (boiling point 130–140° C. @ 0.1 mmHg) to give the title compound as a colourless oil.

NMR (CDCl$_3$) 1.11–1.58 (m, 10H), 2.00 (dt, 2H), 2.43 (dd, 2H), 3.32 (t, 2H), 4.90 (dd, 1H), 4.95 (dd, 1H), 5.75 (m, 1H)

IR (polyethylene) 3078, 2916, 2848, 1772, 1714, 1641

EXAMPLE A8

3-(3-Methylbut-1-y)-3-azabicyclo[3.1.0]hexane-2,4-dione

Sodium hydride (0.11 g) was added to a solution of 3-azabicyclo[3.1.0]hexane-2,4-dione (0.3 g) in dry tetrahydrofuran (10 ml) under a nitrogen atmosphere at room temperature. The suspension was stirred for 5 minutes and 1-iodo-3-methylbutane (0.53 g) was then added in one portion to the reaction mixture. After stirring for two hours at room temperature, dimethylformamide (5 ml) was added and the reaction mixture was stirred for a further 16 hours at room temperature. The reaction mixture was diluted with dichloromethane and then partitioned with water (20 ml). The aqueous phase was extracted with dichloromethane (20 ml) and the combined organic extracts were washed with water (2×20 ml), dried (MgSO$_4$) and evaporated in vacuo. The residue was purified by chromatography on silica gel (50 g) using 25% ethyl acetate/hexane as eluant to give the title compound as a colourless oil.

NMR (CDCl$_3$) 0.89 (d, 6H), 1.29–1.39 (m, 3H), 1.42–1.56 (m, 2H), 2.45 (dd, 2H), 3.36 (d, 2H).

IR (polyethylene) 2958, 2873, 1772, 1715.

EXAMPLE A9

3-(2-Octyl)-3-azabicyclo[3.1.0]hexane-2,4-dione

Sodium hydride (0.11 g) was added to a solution of 3-azabicyclo[3.1.0]hexane-2,4-dione (0.3 g) and 2-bromooctane (0.52 g) in dimethylformamide (5 ml) and the resulting mixture was stirred at room temperature under a nitrogen atmosphere for 48 hours. The mixture was diluted with water (15 ml) and then extracted with toluene (20 ml). The organic extract was washed with water (15 ml), dried (MgSO$_4$) and evaporated in vacuo. The residue was purified by Kugelrohr distillation (boiling point 130–140° C. @ 0.1 mmHg) to give the title compound as a colourless oil.

NMR (CDCl$_3$) 0.87 (t, 3H), 1.03–1.40 (m, 8H), 1.30 (d, 3H), 1.42–1.66 (m, 3H), 1.79–1.95 (m, 1H), 2.42 (dd, 2H), 3.96 (tq, 1H).

MS (thermospray) M/Z [M+H] 224, C$_{13}$H$_{21}$NO$_2$+H requires 224.

IR (polyethylene) 2956, 2916, 2848, 1771, 1715.

EXAMPLE B1

3-n-Octyl-3-azabicyclo[3.1.0]hexane-2,4-dione (alternative route)

A mixture of n-octylamine (24.2 g) and 3-oxabicyclo[3.1.0]hexane-2,4-dione (20.0 g) was heated at 180° C. for 2.5 hours and was then cooled to room temperature. The mixture was distilled in vacuo (boiling point 140–142° C. @ 0.1 mmHg) to give the title compound as a colourless oil.

NMR (CDCl$_3$) 0.83 (t, 3H), 1.15–1.30 (m, 1OH), 1.30–1.40 (m, 2H). 1.40–1.56 (m, 4H), 2.44 (dd, 2H), 3.31 (t, 2H).

MS (thermospray) M/Z [M+NH$_4$] 241, C$_{13}$H$_{21}$NO$_2$+NH$_4$ requires 241

IR (polyethylene) 2955, 2916, 2848, 1771, 1715, 1445, 1395

EXAMPLE B2

3-[2-(Cyclohexen-1-yl)ethyl]-3-azabicyclo[3.1.0]hexane-2,4-dione

A mixture of 2-(cyclohexen-1-yl)ethylamine (0.59 g) and 3-oxabicyclo[3.1.0]hexane-2,4-dione (0.5 g) was heated at 180° C. for 3 hours. The resulting mixture was cooled to room temperature to give the title compound as a yellow solid, m.p. 60–61° C.

NMR (CDCl$_3$) 1.33 (dt, 1H), 1.41–1.65 (m, 5H), 1.87–2.00 (m, 4H), 2.13 (t, 2H), 2.41 (dd, 2H), 3.44 (t, 2H), 5.30–5.37 (m, 1H)

MS (thermospray) M/Z [M+H] 220, C$_{13}$H$_{17}$NO$_2$+H requires 220

IR (polyethylene) 3100, 2915, 2848,1761,1714

EXAMPLE C1

3-(6-Hepten-1-yl)-3-azabicyclo[3.1.0]hexane-2,4-dione

Diethyl azodicarboxylate (0.5 g) was added dropwise over 1 minute to a stirred solution of triphenylphosphine (0.75 g) in tetrahydrofuran (20 ml) at −78° C. under a nitrogen atmosphere. The reaction mixture was stirred for 5 minutes and then 6-hepten-1-ol (0.36 g) was added dropwise over 1 minute, followed by stirring at −78° C. for a further 5 minutes. Neopentanol (0.12 g) was added to the reaction mixture, followed by 3-azabicyclo[3.1.0]hexane-2,4dione (0.32 g) and stirring was continued for a further 5 minutes at −78° C. The reaction mixture was warmed to room temperature and stirred overnight. The volatiles were removed by evaporation in vacuo and the residue was triturated with hexane/dichloromethane and then filtered. The filtrate was evaporated in vacuo and then purified by chromatography on silica gel using 20% ethyl acetate/hexane as eluant. The title compound was obtained as a colourless oil (boiling point 150–160° C. @ 1 mmHg).

NMR (CDCl$_3$) 1.17–1.59 (m, 8H), 1.96–2.08 (m, 2H), 2.45 (dd, 2H), 3.33 (t, 2H), 4.93 (dd, 1H), 4.98 (dd, 1H), 5.78 (m, 1H)

MS (thermospray) M/Z [M+NH$_4$] 225, C$_{12}$H$_{17}$NO$_2$+NH$_4$ requires 225

IR (polyethylene) 3463, 3078, 2937, 2916, 2861, 1771, 1715

EXAMPLE D1

3-(6-Fluorohex-1-yl)-3-azabicyclo[3.1.0]hexane-2,4-dione (a) 3-[6-($^t$Butyldimethylsilyloxy)hex-1-yl]-3-azabicyclo[3.1.0]hexane-2,4dione Sodium hydride (0.55 g, 60% in oil) was added to a stirred solution of 3-azabicyclo[3.1.0]hexane-2,4-dione (1.5 g) and 1-chloro-6-(tert-butyldimethylsilyloxy)-hexane (3.46 g) in dry dimethylformamide (15 ml) at 0° C. under a nitrogen atmosphere. The reaction mixture was warmed to room temperature after the initial effervescence had ceased and was stirred at room temperature for 3 days. Water (20 ml) was added to the reaction mixture and the aqueous mixture was extracted with ether (3×20 ml) and the combined organic extracts were then washed with water (2×40 ml), dried (MgSO$_4$) and evaporated in vacuo. The residue was purified by Kugelrohr distillation to give the subtitle compound as a colourless oil.

NMR (CDCl$_3$) 0.05 (s, 6H), 0.88 (s, 9H), 1.18–1.39 (m, 5H), 1.40–1.58 (m, 5H), 2.45 (dd, 2H), 3.34 (t, 2H), 3.57 (t, 2H)

MS (thermospray) M/Z [M+H] 326, C$_{17}$H$_{31}$NO$_3$Si+H requires 326

IR (polyethylene) 3094, 29511 2915, 2862, 1776,1714

(b) 3-(6-hydroxyhex-1-yl)-3-azabicyclo[3.1.0]hexane-2,4-dione

3-[6-($^t$Butyldimethylsilyloxy)hex-1-yl]-3-azabicyclo[3.1.0]hexane-2,4-dione (from step (a), 2.2 g) was dissolved in 2:1 acetic acid/water (15 ml) and stirred at room temperature for 7 days. The reaction mixture was made alkaline with aqueous sodium bicarbonate solution and then extracted with ether (3×50 ml). The combined ether extracts were dried (MgSO$_4$) and evaporated in vacuo, leaving a yellow oil. The oil was distilled in vacuo and then purified by chromatography on silica using 70% ethyl acetate/hexane as eluant to give the subtitle compound as a colourless oil.

NMR (CDCl$_3$) 1.19–1.43 (m, 5H), 1.44–1.61 (m, 6H), 2.45 (dd, 2H), 3.34 (t, 2H), 3.62 (dt, 2H)

MS (thermospray) M/Z [M+H] 212, C$_{11}$H$_{17}$NO$_3$+H requires 212

IR (polyethylene) 3457, 3096, 2947, 2867,1770,1704, 1694

(c) 3–6-Fluorohex-1-yl)-3-azabicyclo[3.1.0]hexane-2,4dione

Diethylaminosulfurtrifluoride (76mg) was added dropwise to a stirred solution of 3-(6-hydroxyhex-1-yl)-3-azabicyclo[3.1.0]hexane-2,4-dione (from step (b), 100mg) in dichloromethane (2.0 ml) at room temperature under a nitrogen atmosphere. The reaction mixture was stirred overnight at room temperature and water (3 ml) was then added. The reaction mixture was extracted with ether (2×10 ml) and the combined organic extracts were dried (MgSO$_4$) and evaporated in vacuo. The residue was purified by chromatography on silica (5 g) using 40% ethyl acetate/hexane as eluant to give the title compound as a pale yellow oil.

NMR (CDCl$_3$) 1.19–1.75 (m, 10H), 2.44 (dd, 2H), 3.34 (t, 2H), 4.39 (dt, 2H)

MS (thermospray) M/Z [M+H] 214, C$_{11}$H$_{16}$FNO$_2$+H requires 214

IR (polyethylene) 3462.5, 3096, 2945, 2856,1771, 1705

EXAMPLE D2

3-(7,7-Difluorohept-1-yl)-3-azabicyclo[3.1.0]hexane-2,4-dione (a) 3-(7-Hydroxyhept-1-yl)-3-azabicyclo[3.1.0]hexane-2,4-dione Diethyl azodicarboxylate (0.94 g) was added to a mixture of 3-azabicyclo[3.1.0]hexane-2,4-dione (0.5 g), 1,7-heptanediol (2.46 g), triphenylphosphine (1.42 g) and 4 angstrom sieves (1.5 g) in dry tetrahydrofuran (10 ml) under a nitrogen atmosphere. The reaction mixture was stirred at room temperature for 2 days and was then filtered. The solids were washed with ethyl acetate (2×50 ml) and the combined filtrates were evaporated in vacuo. The residue was purified by chromatography on silica using 60–70% ethyl acetate/hexane as eluant, followed by kugelrohr distillation (b.p. 200–220° C. @ 1 mmHg) to give the subtitle compound as a viscous oil.

NMR (CDCl$_3$) 1.18–1.65 (m, 13H), 2.45 (dd, 2H), 3.33 (t, 2H), 3.63 (t, 2H)

MS (thermospray) M/Z [M+H] 226, C$_{12}$H$_{19}$NO$_3$+H requires 226

IR (polyethylene) 3391, 2916, 2848, 1770, 1714.5, 1695

(b) 3-(7-oxohept-1-yl)-3-azabicyclo[3.1.O]hexane-2,4-dione

A solution of dimethylsulfoxide (0.28 ml) in dichloromethane (2 ml) was added dropwise over 5 minutes to a stirred solution of oxalyl chloride (0.16 ml) in dichloromethane (8 ml) at −60° C. under a nitrogen atmosphere. The resulting mixture was stirred for 15 minutes at −60° C. and then 3-(7-hydroxyhept-1 -yl)-3-azabicyclo[3.1.0] hexane-2,4dione (from step
(a), 0.37 g) was added dropwise over 5 minutes. Stirring was continued at −60° C. for a further 15 minutes and then triethylamine (1.15 ml) was added and after a further 5 minutes at −60° C., the reaction mixture was allowed to warm to room temperature. After about 60 minutes, water (10 ml) was added to the reaction mixture and stirring was continued for 10 minutes. The organic phase was separated and the aqueous phase was extracted with dichloromethane (20 ml). The combined organic extracts were dried ($Na_2SO_4$) and evaporated in vacuo to give a yellow oil, which was purified by chromatography on silica (10 g) using 40% ethyl acetate/hexane as eluant to give the subtitle compound as a pale yellow oil.

NMR ($CDCl_3$) 1.20–1.40 (m, 5H), 1.41–1.70 (m, 5H), 2.37–2.51 (m, 4H), 3.34 (t, 2H), 9.75 (s, 1H)

MS (thermospray) M/Z [$M+NH_4$] 241, $C_{12}H_{17}NO_3+NH_4$ requires 241

IR (polyethylene) 3460, 3096, 2949, 2917, 2862, 1770.5, 1714, 1694

(c) 3-(7.7-Difluoro-1-heptyl)-3-azabicyclo[3.1.0]hexane-2,4-dione

Diethylaminosulfurtrifluoride (48 ml) was added dropwise over 5 minutes to a stirred solution of 3-(7-oxohept-1-yl)-3-azabicyclo[3.1.0]hexane-2,4-dione (from step (b), 77mg) in dichloromethane (10 ml) under a nitrogen atmosphere at room temperature and the resulting mixture was stirred at room temperature overnight. Water (5 ml) was added to the reaction mixture, which was then extracted with ether (2×20 ml) and the combined organic extracts were dried ($MgSO_4$) and evaporated in vacuo. The crude product was purified by chromatography on silica (5 g) using 50% ethyl acetate/hexane as eluant to give the title compound.

NMR ($CDCl_3$) 1.20–1.91 (m, 12H), 2.47 (dd, 2H), 3.34 (t, 2H), 5.78 (tt, 1H)

MS (thermospray) M/Z [M+H] 294, $C_{12}H_{17}F_2NO_2+H$ requires 294

IR (polyethylene) 3097, 2918, 2850,1772,1714

EXAMPLE E

Biological Test Result

The compound of Example A3 (and B1) was tested in Test A above. At a dose of 2.5 $\mu g/cm^2$, the compound was found to exhibit 49% repellence. The compound still exhibited 33% repellence after 24 hours.

EXAMPLE F

Insect Repellent Cream

Emulsifying Ointment BP 300 g
3-n-Octyl-3-azabicyclo[3.1.0]hexane-2,4dione 200 g
Phenoxyethanol 10 g
Purified water, freshly boiled and cooled 490 g The cream may be prepared by dissolving the phenoxyethanol in the purified water with the aid of gentle heat. The Emulsifying Ointment is melted and then the phenoxyethanol solution is added to it together with the 3-n-octyl-3-azabicyclo[3.1.0]hexane-2,4dione while the ointment is still warm. The mixture is stirred gently until cold.

In use on humans, the cream is applied to exposed skin to give a thin covering, in the conventional manner.

What is claimed is:

1. An insect- or acarid-repellent formulation comprising a compound of formula I, wherein R is straight or branched chain $C_{2-10}$ alkyl, straight or branched chain $C_{2-10}$ alkenyl, or straight or branched chain $C_{2-10}$ alkynyl; said alkyl, alkenyl and alkynyl are optionally substituted by one or more groups selected from halogen, $C_{4-8}$ cycloalkyl and $C_{4-8}$ cycloalkenyl;
and a suitable adjuvant, diluent or carrier.

2. A formulation of claim 1, wherein R is straight chain $C_{2-10}$ alkenyl.

3. A formulation of claim 2, wherein R is 6-hepten-1-yl.

4. A formulation of claim 1, wherein R is straight chain $C_{2-10}$ alkyl, optionally substituted by chlorine.

5. A formulation of claim 1, wherein R comprises a $C_{4-6}$ cycloalkyl group.

6. A formulation of claim 1 which is a cream or a lotion.
7. A formulation of claim 2 which is a cream or a lotion.
8. A formulation of claim 3 which is a cream or a lotion.
9. A formulation of claim 4 which is a cream or a lotion.
10. A formulation of claim 5 which is a cream or a lotion.
11. A compound of formula I, wherein R is straight or branched chain $C_{2-10}$ alkyl, straight or branched chain $C_{2-10}$ alkenyl, or straight or branched chain $C_{2-10}$ alkynyl; said alkyl, alkenyl and alkynyl are optionally substituted by one or more groups selected from halogen, $C_{4-8}$ cycloalkyl and $C_{4-8}$ cycloalkenyl, with the proviso that R is not n-butyl or n-octyl.

12. A compound of formula IV, wherein $R^d$ is straight or branched chain $C_{2-10}$ alkyl, straight or branched chain $C_{2-10}$ alkenyl, or straight or branched chain $C_{2-10}$ alkynyl; said alkyl, alkenyl and alkynyl are optionally substituted by one or more groups selected from $C_{4-8}$ cycloalkyl and $C_{4-8}$ cycloalkenyl, and said alkyl, alkenyl, alkynyl, cycloalkyl and cycloalkenyl are substituted by one or more hydroxy or oxo.

13. A method of repelling insects or acarids which comprises applying a compound of claim 11 to the exterior of a mammal.

14. The method of claim 13 wherein the mammal is a human, a companion animal or a livestock animal.

15. The method of claim 13 wherein the insects are mosquitoes, gnats or midges.

16. The method of claim 13 wherein the acarids are ticks.

17. The method of claim 14 wherein the mammal is a human, a companion animal or a livestock animal.

18. The method of claim 14 wherein the insects are mosquitoes, gnats or midges.

19. The method of claim 14 wherein the acarids are ticks.

20. A process for preparing a compound of claim 11 which comprises:

(a) reacting the compound of formula II,

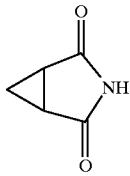

with a compound of formula RX, wherein R is straight or branched chain $C_{2-10}$ alkyl, straight or branched chain $C_{2-10}$ alkenyl, or straight or branched chain $C_{2-10}$ alkynyl; aid alkyl, alkenyl and alkynyl are optionally substituted by one or more groups selected from halogen, $C_{4-8}$ cycloalkyl and $C_{4-8}$ cycloalkenyl and X is halogen, in the presence of a base;

(b) reacting the compound of formula III

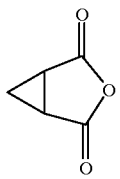

with a compound of formula $RNH_2$, wherein R is as defined above;

(c) reacting the compound of formula II with diethylazodicarboxylate, triphenylphosphine and a compound of formula ROH, wherein R is as defined above, in a Mitsunobu reaction; or (d) reacting a compound of formula IV,

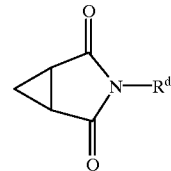

in which $R^d$ has the same definition as R above except that it is substituted by OH or oxo, with diethylaminosulfurtrifluoride to give a corresponding compound of formula I in which each OH or oxo group is replaced with one or two fluorine atoms, respectively.

21. A method of repelling insects or acarids which comprises applying a compound of formula I

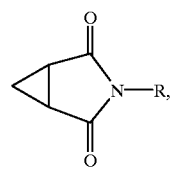

I wherein R is n-butyl or n-octyl to the exterior of a mammal.

* * * * *